United States Patent [19]

Horie et al.

[11] 4,423,130

[45] Dec. 27, 1983

[54] ELECTROPHOTOGRAPHIC LIGHT-SENSITIVE HYDRAZONE MATERIALS

[75] Inventors: Seiji Horie; Junji Nakano; Hideo Sato, all of Asaka, Japan

[73] Assignee: Fuji Photo Film Co., Ltd., Kanagawa, Japan

[21] Appl. No.: 357,112

[22] Filed: Mar. 11, 1982

[30] Foreign Application Priority Data

Mar. 11, 1981 [JP] Japan ............................ 56-33832

[51] Int. Cl.³ .................... G03G 5/06; G03G 5/14
[52] U.S. Cl. .................................. 430/59; 430/58; 430/76; 430/77; 430/78; 430/79; 564/249; 564/251
[58] Field of Search .................. 430/58, 59, 76, 77, 430/78, 79; 564/249, 251

[56] References Cited

U.S. PATENT DOCUMENTS

| | | | |
|---|---|---|---|
| 3,290,147 | 12/1966 | Mattor et al. .................... | 430/78 X |
| 3,765,884 | 10/1973 | Shea ................................ | 430/78 |
| 3,870,516 | 3/1975 | Smith et al. ..................... | 430/58 X |
| 4,150,987 | 4/1979 | Anderson et al. ............... | 430/59 X |
| 4,278,747 | 7/1981 | Murayama et al. .............. | 430/59 X |
| 4,297,426 | 10/1981 | Sakai ................................ | 430/59 |
| 4,338,388 | 7/1982 | Sakai et al. ...................... | 430/59 |
| 4,391,889 | 7/1983 | Mabuchi et al. ................. | 430/59 |

*Primary Examiner*—Roland E. Martin Jr.
*Attorney, Agent, or Firm*—Sughrue, Mion, Zinn, Macpeak & Seas

[57] ABSTRACT

In an electrophotographic light-sensitive material having on a conductive support a light-sensitive layer composed of a charge generating material and a charge transporting material. A hydrazone compound is used as the charge transporting material for providing the light sensitive layer having high sensitivity and less residual surface potential. The light-sensitive layer is stable to oxidation by ozone generated by corona discharging as well as to heat and light, results in less dark decay of the surface potential. Furthermore, the layer shows less deviation in residual potential and sensitivity due to repeated use.

10 Claims, No Drawings

ELECTROPHOTOGRAPHIC LIGHT-SENSITIVE HYDRAZONE MATERIALS

FIELD OF THE INVENTION

This invention relates to an electrophotographic light-sensitive material, and more particularly, to an electrophotographic light-sensitive material having a layer containing a novel charge transporting material.

BACKGROUND OF THE INVENTION

Charge transporting in an electrophotographic light-sensitive material involves the steps of:

(1) Generating an electric charge by light exposure and (2) transporting the electric charge. A selenium light-sensitive plate is an example of a material capable of performing steps (1) and (2). Steps (1) and (2) may be performed by different materials, such as the well known combination of amorphous selenium and poly-N-vinylcarbazole. Systems which perform steps (1) and (2) utilizing different materials is advantageous in that the range of selecting materials used for light-sensitive materials can be enlarged. Accordingly, the electrophotographic characteristics such as the sensitivity of the light-sensitive materials, the receptive potential of the light-sensitive materials, etc., are improved. Furthermore, materials suitable for making light-sensitive coatings or layers can be selected over a wide range.

Examples of photoconductive materials for light-sensitive materials usually used in electrophotographic systems, include inorganic materials such as selenium, cadmium sulfide and zinc oxide.

U.S. Pat. No. 2,297,691 to Carlson, discloses an electrophotographic material composed of a support having coated thereon a material which shows an insulating property in the dark and changes its electric resistance in accordance with the irradiated amount of light during image exposure. After being subjected to a dark adaptation for a proper period of time, the photoconductive material is generally uniformly charged, on the surface, in the dark. Then, the photoconductive material is image-exposed to a pattern of light irradiation. The irradiation reduces the surface charge in proportion of the relative energy included in the various portions of the pattern of light irradiation. The surface charge remaining on the surface of the layer of the photoconductive material (light-sensitive layer) or the electrostatic latent image thus formed on the surface is converted into a visible image by contacting the surface thereof with a proper electroscopic material, i.e., a toner. The toner can be attached onto the surface of the light-sensitive layer in proportion to the charge pattern in both the state contained in an insulating liquid and the state contained in a dry carrier. The toner image thus formed can be fixed by a known means such as heating, pressing, or a solvent vapor. The toner can be alternatively transferred onto a secondary support (e.g., a paper, film, etc.,) and then fixed. The foregoing electrostatic latent image can be transferred onto a secondary support and developed. An electrophotographic process is an image-forming process which involves forming images in a manner such as described above.

Light-sensitive materials used in such electrophotographic processes must have such fumdamental characteristics as: (1) light-sensitive material can be charged at a proper electric potential in the dark, (2) it lets escape less of the electric charge charged on the surface thereof in the dark, and (3) it discharges quickly by the irradiation of light. Inorganic materials generally used for photoconductive materials have various advantages and disadvantages. Selenium which is widely used at present sufficiently satisfies the above-mentioned factors (1)-(3). However, production costs are high, and the material has poor flexibility, making it difficult to form a belt from such a material. The material must be handled with great care since it is very sensitive to heat and mechanical impact. Cadmium sulfide and zinc oxide are also used as a light-sensitive materials which are dispersed in a resin binder. However, such a light-sensitive material is poor in such properties as smoothness, hardness, tensile strength, abrasion resistance, etc.

Recently, electrophotographic light-sensitive materials using various organic materials have been proposed for eliminating the disadvantages of inorganic materials. Such materials have been practically used. For example, there is a light-sensitive material composed of poly-N-vinylcarbazole and 2,4,7-trinitrofluoren-9-one (see, U.S. Pat. No. 3,484,237), poly-N-vinylcarbazole sensitized by a pyrylium salt series dye (see, Japanese Patent Publication No. 25,658/'73), a light-sensitive material composed of an eutectic complex of a dye and a resin as the main component (see, Japanese Patent Application (OPI) No. 10,735/'72), etc.

Other recently proposed materials include: a high-sensitive electrophotographic light-sensitive material composed of a combination of a material generating an electric charge by the action of light (hereinafter, referred to as a charge generating material) and a material capable of transporting the charge thus generated (hereinafter, referred to as a charge transporting material). For example, U.S. Pat. No. 3,791,826 discloses a light-sensitive material composed of a charge generating layer and a charge transporting layer formed thereon. U.S. Pat. No. 3,573,906 discloses a light-sensitive material composed of a charge transporting layer and a charge generating layer formed thereon. U.S. Pat. No. 3,764,315 discloses a light-sensitive material having a light-sensitive layer formed by dispersing a charge generating material in a charge transporting material. In the light-sensitive materials of this type, many useful charge generating materials have been proposed. However, no practical useful charge transporting materials have been proposed at present. An excellent charge transporting material can sufficiently transmit light of wave length capable of generating a charge from a charge generating material to the charge generating material. The material, when charged, can maintain sufficient potential, and the material can quickly transport the charge generated by a charge generating material.

SUMMARY OF THE INVENTION

As a result of various investigations, the inventors have discovered that the hydrazone compounds shown by general formula I, II or III described below are actually useful in practical applications of charge transporting materials for electrophotographic light-sensitive materials.

The hydrazone compounds shown by general formula I described below are not novel compounds and it is disclosed in U.S. Pat. No. 3,765,884 that the hydrazone materials are used as photoconductive materials for electrophotography. However, it must be noticed that the compounds shown by general formula I have no or almost no function as a photoconductive material but function as a charge transporting material in this invention. In order to function as a photoconductive material, the material must be excited by absorbing irradiated light. However, the compounds shown by general formula I show little absorption in the visible range. Accordingly, the compounds must contain a sensitizer for practical use. Furthermore, it should be noted that the sensitivity of the compounds is low even when the compounds are used together with sensitizers. On the other hand, when the compounds shown by general formula I are used for light-sensitive material as a combination with charge generating materials, they have high sensitivity, never supposed by conventional technical knowledge.

Examples of using hydrazone compounds as electrophotographic light-sensitive materials are described in U.S. Pat. Nos. 3,717,462 and 4,150,987; Japanese Patent Application (OPI) Nos. 52,063/'80, 52,064/'80, etc. However, in these examples, condensed polycyclic materials or N-alkylamino substitution compounds are used, and thus, these light sensitive materials have defects of low oxidation resistance to ozone formed by corona discharging, low stability to light and heat, greater dark decay, etc. These disadvantages are fately inferior in the above-described conventional light sensitive materials.

The inventors previously discovered that the electrophotographic light-sensitive materials havine light-sensitive layers containing N-arylamino substitution compounds have greatly overcome such defects shown in the conventional light sensitive materials. In addition they had high sensitivity, less residual potential which causes fog, and processed less deviation of the residual potential and sensitivity caused by repeated use, and were excellent in durability. Patent application were filed on the inventions as Japanese Patent Application Nos. 85,495/'80 and 180,148/'80.

In accordance with the present invention, there are provided electrophotographic light-sensitive materials having excellent characters as in the foregoing inventions of Japanese Patent Application Nos. 85,495/'80 and 180,148/'80, using hydrazone derivatives having novel structures.

An object of this invention is to provide an electrophotographic light-sensitive material having an electrophotographic light-sensitive layer containing a novel charge transporting material.

Another object of this invention is to provide an electrophotographic light-sensitive material having an electrophotographic light-sensitive layer having high sensitivity which gives less residual potential.

Still another object of this invention is to provide an electrophotographic light-sensitive material having a stable electrophotographic light-sensitive layer which has high stability to oxidation by ozone formed by corona discharging, light, and heat; causes less dark decay of the surface potential; shows less increase and deviation of the residual potential by the repeated use thereof; and shows less deviation of sensitivity.

A further object of this invention is to provide an electrophotographic light-sensitive material having an electrophotographic light-sensitive layer containing a charge transporting material which can be prepared using a raw material having no or little toxicity. The resulting photographic light-sensitive material having no or little electrotoxicity and therefore being safe in handling and in waste disposal thereof.

A still further object of this invention is to provide a stable charge transporting layer which has high film strength, is excellent in homogeneity, and shows less deterioration by fatigue. Yet another object of the invention is the production of electrophotographic light-sensitive material having a light-sensitive layer containing the compound represented by following general formula I, II or III:

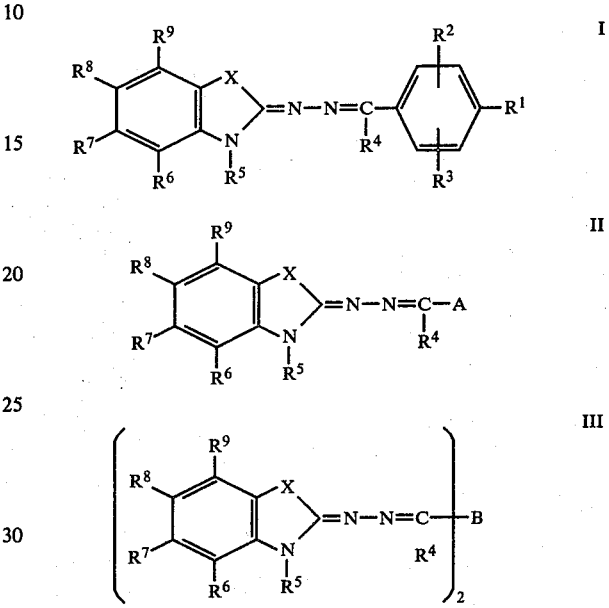

wherein

X represents an oxygen atom, a sulfur atom, a selenium atom, an imino group which may be substituted, or a methylene group which may be substituted. The substituent is an alkyl group having 1 to 18 carbon atoms or an aralkyl group having 7 to 16 carbon atoms.

$R^1$ represents an alkoxy group, an aralkyloxy group, or a substituted amino group shown by

(wherein $R^{10}$ and $R^{11}$, which may be the same or different, each represents an alkyl group which may be substituted, a phenyl group which may be substituted, or a group capable of forming a heterocyclic ring containing a nitrogen atom when $R^{10}$ and $R^{11}$ combine with each other);

$R^2$ and $R^3$ independently represent a hydrogen atom, a halogen atom, an alkyl group, or a lower alkoxy group;

$R^4$ represents a hydrogen atom, an alkyl group, or a phenyl group which may be substituted;

$R^5$ represents an alkyl group which may be substituted;

$R^6$, $R^7$, $R^8$, and $R^9$, independently represent an alkyl group which may be substituted, a phenyl group which may be substituted, an alkoxy group which may be substituted, an aralkyloxy group which may be substituted, a hydrogen atom, a halogen atom, or an amino group shown by

(wherein $R^{12}$ and $R^{13}$ represent a hydrogen atom or the group shown by foregoing $R^{10}$ and $R^{11}$), said $R^6$, $R^7$, $R^8$ and $R^9$ may further combine with each other to form a condensed carbon ring or a condensed heterocyclic ring;

A represents a monocyclic heterocyclic 5-membered ring, a condensed heterocyclic 5-membered ring or a condensed heterocyclic 6-membered ring shown by the following formula

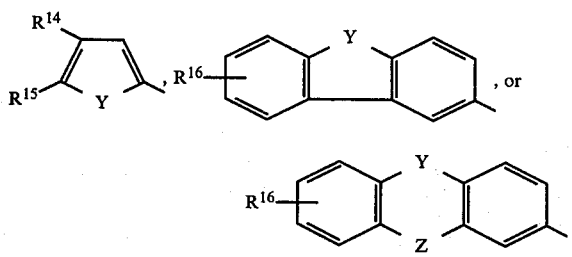

(wherein Y and Z, independently represent a sulfur atom, an oxygen atom or a group shown by N-$R^{17}$ (wherein $R^{17}$ is an alkyl group having 1-4 carbon atoms), $R^{14}$ and $R^{15}$ independently represent a hydrogen atom, an alkyl group, an alkoxy group, or groups capable of forming a benzene ring or a naphthalene ring by combining with each other, and $R^{16}$ represents a hydrogen atom, an alkyl group, an alkoxy group, an aryloxy group, an acyl group, an alkoxycarbonyl group, an aryloxycarbonyl group, a halogen atom, a monoalkylamino group, a dialkylamino group, an amido group, or a nitro group, said groups each may have a substituent which are the same as shown by $R^{10}$ or $R^{11}$ described above; and B represents an aryl group or a substituted aryl group.

DESCRIPTION OF THE PREFERRED EMBODIMENTS

Now, preferred examples of X in general formulae I, II and III are an oxygen atom, a sulfur atom, a selenium atom, an alkylimino group, a dimethylmethylene group, etc. The alkyl group of the alkylimino group is an alkyl group having 1-8 carbon atoms. A particularly preferred example of X is a sulfur atom.

As the alkoxy group or aralkyloxy group shown by $R^1$ of general formula I, there are alkoxy groups having 1-12 carbon atoms and aralkyloxy groups having 7-18 carbon atoms. Preferred examples of these groups are a methoxy group, an ethoxy group, a propoxy group, a butoxy group, an octyloxy group, and a benzyloxy group.

When $R^1$ is the substituted amino group shown by

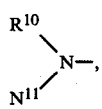

as $R^{10}$ and $R^{11}$, there are an unsubstituted alkyl group having 1-12 carbon atoms, such as methyl group, ethyl group, propyl group, butyl group, etc., and an alkyl group of 1-12 carbon atoms having the following substituent.

As the substituent for the substituted alkyl groups shown by $R^{10}$ and $R^{11}$, there are an alkoxy group having 1-4 carbon atoms, an aryloxy group having 6-12 carbon atoms, a hydroxy group, an aryl group having 6-12 carbon atoms, a cyano group, and a halogen atom. Preferred examples of the substituted alkyl groups shown by $R^{10}$ and $R^{11}$ are, for example, (a) an alkoxyalkyl group such as methoxymethyl group, methoxyethyl group, ethoxymethyl group, ethoxypropyl group, methoxybutyl group, propoxymethyl group, etc.; (b) an aryloxyalkyl group such as phenoxymethyl group, phenoxyethyl group, naphthoxymethyl group, phenoxypentyl group, etc.; (c) a hydroxyalkyl group such as hydroxymethyl group, hydroxyethyl group, hydroxypropyl group, hydroxyoctyl group, etc.; (d) an aralkyl group such as benzyl group, phenethyl group, ω,ω-diphenylalkyl group, etc.; (e) a cyanoalkyl group such as cyanomethyl group, cyanoethyl group, cyanopropyl group, cyanobutyl group, cyanooctyl group, etc.; and (f) a haloalkyl group such as chloromethyl group, bromoethyl group, chloroethyl group, bromophenyl group, chlorooctyl group, etc.

Also, the phenyl groups shown by $R^{10}$ and $R^{11}$ may have a substituent and preferred examples of the substituent for the substituted phenyl groups are (a) an alkyl group having 1-12 carbon atoms, (b) an alkoxy group having 1-4 carbon atoms, (c) an aryloxy group having 6-7 carbon atoms, (d) an acyl group having 2-8 carbon atoms, (e) an alkoxycarbonyl group having 2-5 carbon atoms, (f) a halogen atom, (g) a monoalkylamino group having a substituent of 1-4 carbon atoms, (h) a dialkylamino group having a substituent of 1-4 carbon atoms, (i) an amido group having 2-4 carbon atoms, and (j) a nitro group.

More particularly, (a) preferred examples of the alkyl group having 1-12 carbon atoms as the substituent of the substituted phenyl groups shown by $R^{10}$ and $R^{11}$ are methyl group, ethyl group, straight chain or branched propyl group, butyl group, pentyl group, and hexyl group; (b) preferred examples of the alkoxy group having 1-4 carbon atoms are methoxy group, ethoxy group, propoxy group, and butoxy group; (c) preferred examples of the aryloxy group are phenoxy group, o-tolyloxy group, m-tolyloxy group, and p-tolyloxy group; (d) preferred examples of the acyl group are acetyl group, propionyl group, benzoyl group, o-toluoyl group, m-toluoyl group and p-toluoyl group; (e) preferred examples of the alkoxycarbonyl group having 2-5 carbon atoms are methoxycarbonyl group, ethoxycarbonyl group, propoxycarbonyl group, and butoxycarbonyl group; (f) preferred examples of the halogen atom are chlorine atom, bromine atom, and fluorine atom; (g) preferred examples of the monoalkylamino group substituted by an alkyl group having 1-4 carbon atoms are methylamino group, ethylamino group, and butylamino group; (h) practical examples of the dialkylamino group substituted by an alkyl group having 1-4 carbon atoms are dimethylamino group, diethylamino group, dipropylamino group, dibutylamino group, and N-methyl-n-ethylamino group; (i) preferred examples of the amido group are acetamido group, propionamido group, etc.; and (j) another practical substituent is a nitro group.

As the heterocyclic rings formed by the combination of $R^{10}$ and $R^{11}$, the heterocyclic rings shown by following structural formulae are preferred;

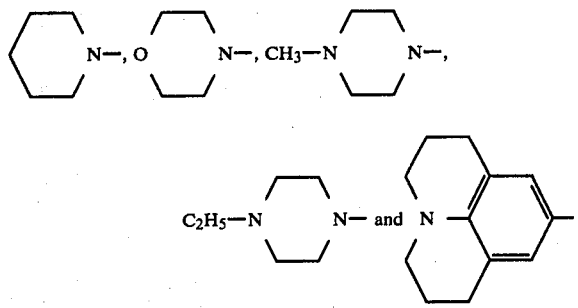

(as a group corresponding to

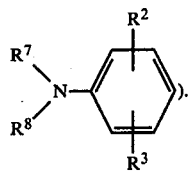

).

It is preferred that $R^1$ be a substituted amino group in the case where $R^{10}$ and $R^{11}$ are methyl group, ethyl group, benzyl group, phenyl group, or tolyl group. Particularly preferred examples of the substituted amino group shown by $R^1$ are a dimethylamino group, a diethylamino group, a dibenzylamino group, a diphenylamino group, an N-ethyl-N-phenylamino group, etc. Preferred examples of $R^2$ and $R^3$ are a hydrogen atom; a halogen atom such as chlorine atom, bromine atom, fluorine atom, etc.; an alkyl group having 1-4 carbon atoms, such as methyl group, ethyl group, propyl group, butyl group, etc.; and an alkoxy group having 1-4 carbon atoms, such as methoxy group, ethoxy group, propoxy group, butoxy group, etc. Preferred examples of these groups are a hydrogen atom, a methyl group, a methoxy group, etc.

Practical examples of $R^4$ are a hydrogen atom; an alkyl group having 1-4 carbon atoms, such as methyl group, ethyl group, propyl group, butyl group, etc., or a phenyl group having or not having substituent. The phenyl group having substituent is the phenyl group having substituent shown by $R^{10}$ or $R^{11}$ as described above. Preferred examples of $R^4$ are a hydrogen atom, a methyl group, an ethyl group, a phenyl group, and a p-(dimethylamino)phenyl group.

The alkyl group having or not having substituent shown by $R^5$ is the same alkyl group which may be substituted as shown by $R^{10}$ or $R^{11}$ described above.

$R^6$, $R^7$, $R^8$ and $R^9$ are an alkyl group which may be substituted and a phenyl group which may be substituted, which are same groups as shown by $R^{10}$ or $R^{11}$ described above. Other examples of these groups are a hydrogen atom; a halogen atom such as chlorine atom, bromine atom, fluorine atom, etc.; an alkoxy group having 1-12 carbon atoms, such as methoxy group, ethoxy group, propoxy group, butoxy group, octyl group, benzyloxy group, etc.; an aralkyloxy group having 1-12 carbon atoms, such as benzyloxy group, phenethyloxy group, etc.; and the amino group shown by

(wherein $R^{12}$ and $R^{13}$ represent a hydrogen atom or the same group as the alkyl or phenyl group which may be substituted shown by $R^{10}$ or $R^{11}$.

$R^6$, $R^7$, $R^8$ and $R^9$ may be the same or different and they may form a condensed carbon ring such as naphthalene or a condensed heterocyclic ring, such as quinoline, N-ethylcarbazole, benzofuran ring, by combining with each other. In the groups shown by $R^6$, $R^7$, $R^8$ and $R^9$, a hydrogen atom is particularly preferred.

Preferred examples of $R^{14}$ and $R^{15}$ of

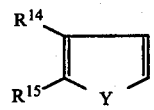

are a hydrogen atom; an alkyl group having 1-4 carbon atoms, such as methyl group, ethyl group, propyl group, butyl group, etc.; an alkoxy group having 1-4 carbon atoms, such as methoxy group, ethoxy group, propoxy group, butoxy group, etc.; and groups capable of forming a benzene ring or a naphthalene ring by the combination of $R^{14}$ and $R^{15}$.

Preferred examples of $R^{16}$ in the condensed heterocyclic ring

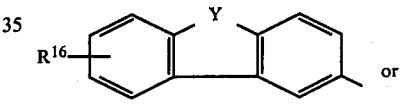

are a hydrogen atom; the alkyl group which may be substituted same as the alkyl group having or not having substituent shown by $R^{10}$ or $R^{11}$ described above, an alkoxy group having 1-4 carbon atoms, an aryloxy group having 6-10 carbon atoms, an acyl group having 2-11 carbon atoms, an alkoxycarbonyl group having 2-5 carbon atoms, an aryloxycarbonyl group having 7-11 carbon atoms, a monoalkylamino group having 1-4 carbon atoms, a dialkylamino group having 1-4 carbon atoms, an amido group having 2-9 carbon atoms, and a nitro group; these groups may have substituents.

More particularly, preferred examples of the alkoxy group having 1-4 carbon atoms shown by foregoing $R^{16}$ are a methoxy group, an ethoxy group, a propoxy group, a butoxy group, etc.; preferred examples of the aryloxy group are a phenoxy group, an o-tolyloxy group, a m-tolyloxy group, and a p-tolyloxy group; preferred examples of the acyl group are an acetyl group, a propionyl group, a benzoyl group, an o-toluoyl group, a m-toluoyl group, and a p-toluoyl group; preferred examples of the alkoxycarbonyl group having 2-5 carbon atoms are a methoxycarbonyl group, an ethoxycarbonyl group, a propoxycarbonyl group, and a butoxycarbonyl group; preferred examples of the aryloxycarbonyl group having 7-11 carbon atoms are a phenoxycarbonyl group, an o-tolyloxycarbonyl group, a m-tolyloxycarbonyl group, and a p-tolyloxycarbonyl group; preferred examples of the halogen atom are chlorine atom, bromine atom, fluorine atom; preferred examples of the monoalkylamino group substituted by an alkyl group having 1-4 carbon atoms are a methylamino group, an ethylamino group, and a butylamino group; preferred examples of the dialkylamino group substituted by an alkyl group having 1-4 carbon atoms are a dimethylamino group, a diethylamino group, a dipropylamino group, a dibutylamino group, and an N-methyl-N-ethylamino group; preferred examples of the amido group are an acetamido group and a propionamido group; and other substituent is a nitro group.

Preferred examples of the heterocyclic 5-membered ring shown by A are a 2-furyl group, a 2-thienyl group, a 1-methyl-2-pyrrolyl group, and a 5-methyl-2-thienyl group; practical examples of the condensed heterocyclic 5-membered ring shown by A are a 2-benzo[b]thienyl group, a 2-naphtho[2,3-b]thienyl group, a 9-ethylcarbazol-2-yl group, a dibenzothiophen-2-yl group; and preferred examples of the condensed heterocyclic 6-membered ring shown by A are a 2-phenoxathiinyl group, a 10-phenoxazin-3-yl group, and a 10-ethylphenothiazin-3-yl group as shown by the following formulae;

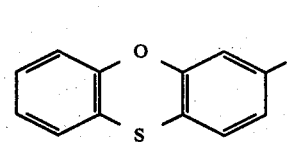
2-phenoxathiinyl group

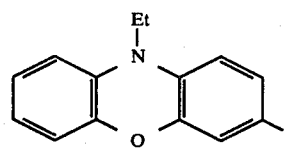
10-ethylphenoxazin-3-yl group

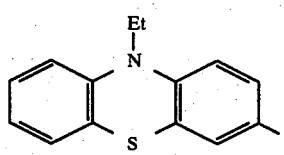
10-ethylphenothiazin-3-yl group

Among these groups, preferred examples are a 5-methyl-2-thienyl group, a 2-benzo[b]thienyl group, a 9-ethylcarbazol-2-yl group, a dibenzothiophen-2-yl group, and 10-ethylphenothiazin-3-yl group.

Preferred examples of B are a phenyl group and a naphthyl group. When these groups have a substituent, the substituent is same as the group shown by $R^2$ or $R^3$.

Preferred examples of the hydrazone compounds shown by general formula I, II or III are shown below:

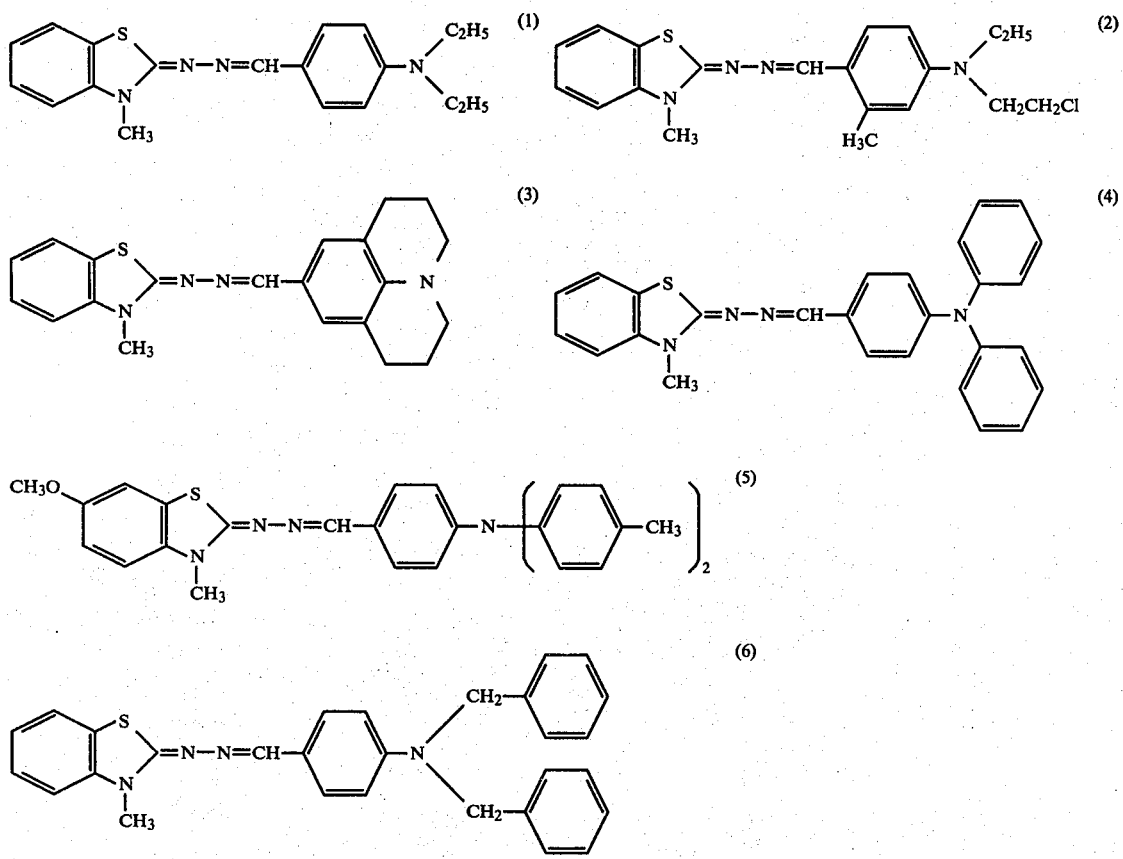

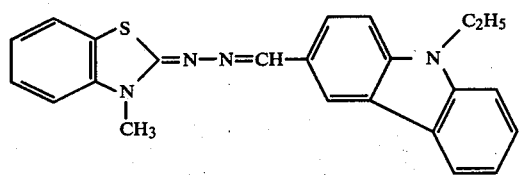 (7)
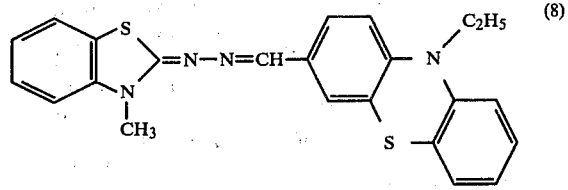 (8)
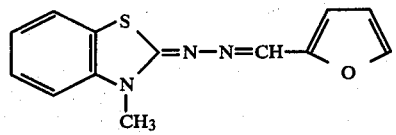 (9)
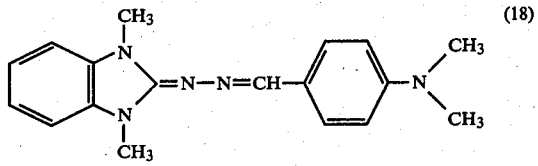 (10)
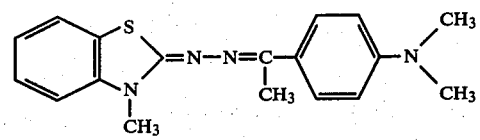 (11)
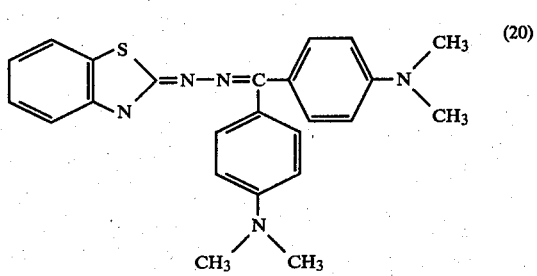 (12)
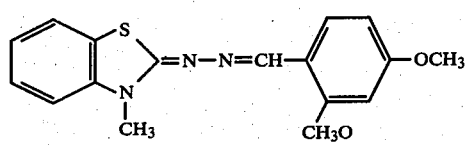 (13)
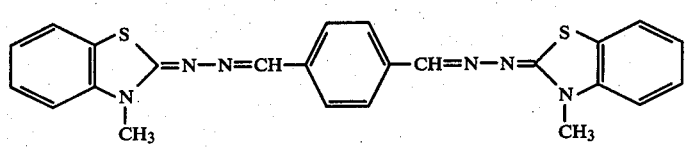 (14)
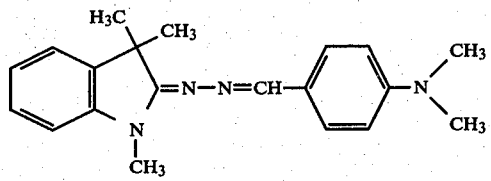 (15)
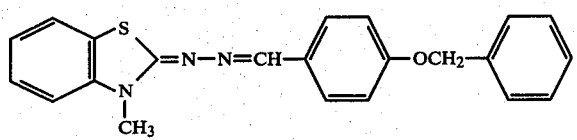 (16)
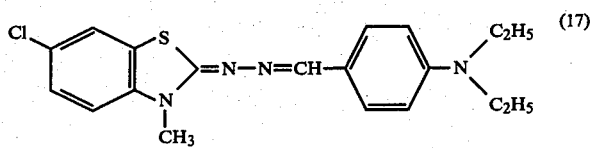 (17)
(18)
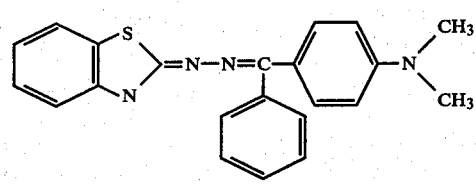 (19)
(20)
The hydrazone compounds shown by general formula I, II or III can be easily prepared by known methods. That is, they can be prepared by dehydration-condensing aldehydes or ketones corresponding to the heterocyclic hydrazones in a solvent with the addition of, if necessary, a small amount of an acid (acetic acid or an inorganic acid) as a condensing agent. As the solvent used in the reaction, there are alcohols such as methanol, ethanol, etc.; aromatic hydrocarbons such as benzene, xylene, etc.; dioxane; tetrahydrofuran; N,N-dimethylformamide, etc. They can be used solely or as a mixture of them. These processes for producing the hydrazone compounds shown by general formula I, II or III are described in U.S. Pat. No. 3,765,884, Japanese Patent Application Nos. 85,495/'80 and 180,148/'80.

By using the compounds shown by general formula I, II or III as a charge transporting material, it is possible to improve the property of film with respect to durability, charging characteristics, and residual potential characteristics of the electrophotographic light-sensitive layer containing the charge transporting material. Also, since the compounds shown by general formula I, II or III have excellent compatibility with various high molecular binders, the electrophotographic light-sensitive layer does not become turbid or opaque even when a large amount of the charge transporting material is used with the high molecular binder in the light-sensitive layer. Thus, the selection range and the amount of the high molecular binder can be broadened for the charge transporting material and hence an electrophotographic light-sensitive material having preferred charge transporting property can be produced. Furthermore, the film produced is capable of responding to any particular purpose and use.

The compounds shown by general formula I, II or III are advantageous in that the compounds can provide effective electrophotographic light-sensitive materials in combination with optional charge generating materials.

Examples of the charge generating materials used in this invention are as follows:

(1) Selenium and selenium alloys.
(2) Inorganic photoconductors such as CdS, CdSe, CdSSe, ZnO, and ZnS.
(3) Phthalocyanine pigments such as metal phthalocyanine and non-metal phthalocyanine.
(4) Azoic dyes such as monoazo dyes and disazo dyes.
(5) Perylene series pigments such as perylenic acid anhydride and perylenic acid imide.
(6) Indigoid dyes.
(7) Quinacridone pigments.
(8) Polycyclic quinones such as anthraquinones, pyrenequinones, anthanthrones, and flavanthrones.
(9) Bisbenzimidazole pigments.
(10) Cyanine dyes.
(11) Squaric compounds.
(12) Indanthrone pigments.
(13) Xanthene dyes.
(14) Charge transferring complexes composed of electron donative materials such as poly-N-vinylcarbazole and electron acceptors such as trinitrofluorenone.
(15) Eutectic complexes composed of pyrylium salt dyes and polycarbonate resins.
(16) Amorphous silicon, etc.

A high molecular binder used together with the compounds shown by general formula I, II or III in this invention is a film-forming high molecular weight polymer or copolymer having a hydrophobic property, a high permittivity, and a good electric insulating property. Preferable examples of such polymers or copolymers are as follows:

(1) Polystyrene resins.
(2) Polyvinyl chloride resins.
(3) Polyvinylidene chloride resins.
(4) Polyvinyl acetate resins.
(5) Acrylic resins.
(6) Methacrylic resins.
(7) Styrene-butadiene copolymers.
(8) Vinylidene chloride-acrylonitrile copolymers.
(9) Vinyl chloride-vinyl acetate copolymers.
(10) Silicone resins.
(11) Polyester resins.
(12) Polycarbonate resins.
(13) Styrene-alkyd resins.
(14) Silicone-alkyd resins.
(15) Phenol-formaldehyde resins.

These high molecular binders are used solely or as a mixture of them although the binders used in this invention are not limited to these materials.

The electrophotographic light-sensitive material of this invention is obtained by uniformly dispersing or dissolving the above-described charge transporting material in a high molecular binder together with a charge generating material and forming a layer of the dispersion or solution on a conductive support. However, when an organic dye is used as the charge generating material, it is preferable to use the organic dye in an aggregated state and mix the aggregated dye with the charge transporting material in a heterogeneous state since the light-sensitive material prepared using these materials is highly sensitive and possesses excellent durability. Furthermore, in this invention, the light-sensitive material having the most excellent electrophotographic characteristics is obtained when employing a two-layer structure. The structure is produced by forming a charge generating layer composed of a charge generating material as a main component on a conductive support through, if necessary, an interlayer and forming a charge transporting layer composed of the charge transporting material as a main component adjacent to the charge generating layer. The light-sensitive material is obtained by forming a charge transporting layer having dispersed therein the fine particles of a charge generating material on a conductive support. If necessary, an interlayer can be effectively used in this invention.

Also, when employing the two-layer structure, the selection of the upper layer from the charge generating layer and the charge transporting layer is determined by the selection of the polarity of the charge to be formed on the surface of the light-sensitive material. That is when negatively charging the electrophotographic light-sensitive layer, it is advantageous (for obtaining desired characteristics) to select the charge transporting layer as the upper layer.

In this invention, it is advantageous to form the charge transporting layer as the upper layer since the compounds shown by general formula I, II or III are predominant for positive charge transferring.

When a two-layer structure composed of the separate charge generating layer and charge transporting layer is employed for the electrophotographic light-sensitive material of this invention, the charge generating layer can be formed on a conductive support directly or after forming thereon an interlayer such as an adhesive layer or a barrier layer by:

(1) vacuum deposition,
(2) coating a solution of the charge generating material dissolved in a proper solvent, or (3) coating a dispersion prepared by finely dispersing the charge generating material in a dispersion medium using a ball mill, homogenizer, etc., together with, if necessary, a high molecular binder. In this case, the high molecular binder used for the layer may be the same material as the binder used for the charge transporting layer.

The thickness of the charge generating layer constituting the light-sensitive material of this invention may be optional but is preferably 0.05-5 μm, more preferably 0.1-3 μm.

The compound of this invention shown by general formula I, II or III is used together with a high molecular binder. It is preferred that the proportion of the high molecular binder as 0.8-4 parts by weight per 1 part by weight of the compound of this invention. When using the charge generating material and the charge transporting material in a same layer, it is preferable to use 0.8-4 parts by weight of the high molecular binder and 0.1-2 parts by weight of the charge generating material per one part by weight of the compound (the charge transporting material) of this invention.

Also, in the case of employing the charge generating layer composed of a dispersion of a charge generating material in a high molecular binder, it is preferable to use the high molecular binder in a range of less than 10 parts by weight per one part by weight of the charge generating material.

Example of the conductive support used for the light-sensitive materials of this invention, include a paper or a plastic material support subjected to a conductive treatment by applying a conductive compound or a metallic thin layer on the surface, a metallic sheet having, if necessary, a layer of palladium, aluminum, etc., on the surface thereof by vacuum deposition or coating and an aluminum sheet.

In this invention an interlayer may be formed between the support and the charge generating layer or the charge transporting layer, or further a light-sensitive layer containing the charge generating material and the charge transporting material. Materials used for forming such interlayers include high molecular binders as well as organic high molecular weight compounds such as casein, gelatin, starch, polyvinyl alcohol, polyvinyl acetate, ethyl cellulose, carboxymethyl cellulose, etc., and metal oxides such as aluminum oxide.

The invention will further be explained by referring to the following examples but the invention is not limited to these examples. In the following examples, all parts are by weight unless otherwise indicated.

Synthesis examples 1-7:

Synthesis of Compound (1) of this invention.

In a mixture of 500 ml of ethanol and 100 ml of acetic acid were dissolved 30 g of 3-methyl-2-benzothiazolinonehydrazone and 30 g of p-(diethylamino)-benzaldehyde. The solution thus prepared was refluxed for 2 hours. After cooling the reaction mixture, the yellow precipitates formed were recovered by filtration, dried, and then recrystallized from ethanol to provide 43 g of Compound (1), N-[p-(diethylamino)benzylidene]-N'-(3-methyl-2-benzothiazolidene)hydrazine.

Compound (I)

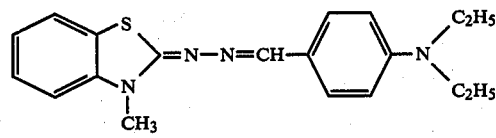

Melting point: 139.5°-140.3° C.

Yield: 77%.

Other compounds of this invention could be also prepared in the manner described above using the corresponding hydrazines and aldehydes or ketones.

The examples of the compounds prepared and the melting points thereof are shown below:

Compound (2)　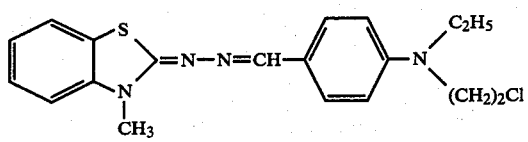　154~155° C.

Compound (4)　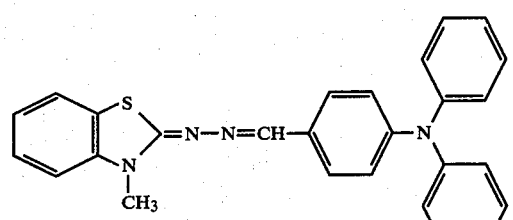　179~181° C.

Compound (7)　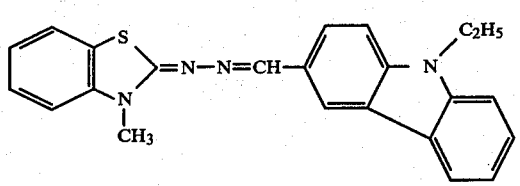　173~174° C.

Compound (8) 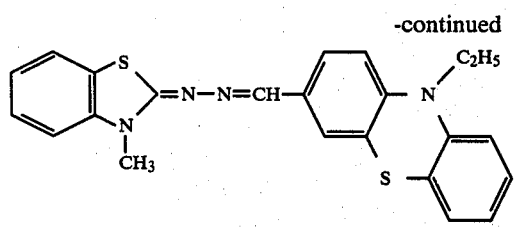  160.5~162° C.

Compound (12) 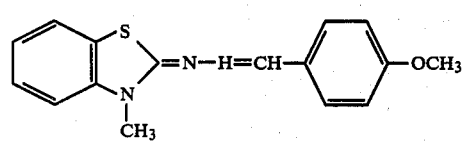  142.7~143.2° C.

Compound (10) 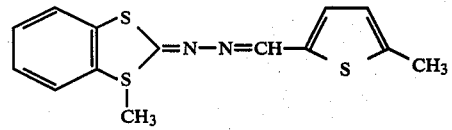  166~166.7° C.

EXAMPLE 1

On the surface of a grained aluminum sheet having a thickness of 0.3 mm was found a selenium layer 0.4 μm thick by vacuum deposition to form a charge generating layer. Then a solution prepared by dissolving 4.6 parts of Compound (1) and 5.4 parts of a polycarbonate of bisphenol A in 78 parts of 1,2-dichloromethane was coated on the layer using a wire round rod followed by drying to form a charge transporting layer 8 μm thick. Accordingly, an electrophotographic light-sensitive material having a double-layer type electrophotographic light-sensitive layer was prepared.

When using an electrostatic copying paper test machine (SP-428-type, made by Kawaguchi Denki K.K.), the light-sensitive material was negatively charged by corona discharging of −5 KV. After irradiating the surface with a tungsten lamp with a color temperature of 3000° K. so that the surface illuminance became 4.5 luxes, a half decay exposure amount $E_{50}$ (lux.sec.) was determined by measuring the time required to decay the initial surface potential to half. The exposure was 10 lux.sec. The two steps of charging and light exposure were repeated 3,000 times but the $E_{50}$ value scarcely changed.

EXAMPLES 2-12

By following the same procedure as in Example 1 except that Compounds (2), (3), (4), (6), (7), (8), (9), (10), (11), (12), and (13) were used in place of compound (1) in Example 1, double layer structure light-sensitive materials were prepared. With these samples, the half decay exposure amounts by negative charging were measured. The results are shown in the following table.

| Example | Compound | $E_{50}$ (lux. sec.) |
| --- | --- | --- |
| 2 | (2) | 9 |
| 3 | (3) | 13 |
| 4 | (4) | 11 |
| 5 | (6) | 10 |
| 6 | (7) | 12 |
| 7 | (8) | 25 |
| 8 | (9) | 52 |
| 9 | (10) | 15 |
| 10 | (11) | 19 |
| 11 | (12) | 13 |
| 12 | (13) | 9 |

EXAMPLE 13

To 660 parts of dichlorochromethane was added 5 parts of β-type copper phthalocyanine. After dispersing the additive with ultrasonic wave treatment, 40 parts of a polycarbonate of bisphenol A and 40 parts of Compound (1) were dissolved in the dispersion to provide a coating composition.

The coating composition was coated on a conductive transparent support (a polyethylene terephthalate film, 100 μm thick, having formed thereon a vapor deposited layer of indium oxide, having a surface electric resistance of $10^3\Omega$) using a wire round rod and dried to provide an electrophotographic light-sensitive material having an electrophotographic light-sensitive layer 9.5 μm thick.

When the light-sensitive material was positively charged by corona discharging of +5 KV and then the half decay exposure amount was measured as in Example 1, the $E_{50}$ value was 18 lux.sec.

EXAMPLE 14

To 260 parts of dichloromethane were added 2 parts of Chlorodian Blue shown by the structure described below and 2 parts of a polycarbonate of bisphenol A. The mixture was pulverized and mixed in a ball mill to provide a coating composition and the coating composition was coated on a conductive transparent support (a polyethylenetetraphthalate film of 100 μm having formed on the surface thereof a vapor deposited layer of indium oxide, and having a surface resistance of $10^3\Omega$) using a wire round rod and dried to form a charge generating layer of 1 μm thick.

Then, a solution prepared by dissolving 2 parts of Compound (2) and 4 parts of a polycarbonate of bisphenol A in 60 parts of dichloromethane was coated on the charge generating layer and dried to form a charge transporting layer about 8 μm thick.

When on the electrophotographic light-sensitive material having the double layer light-sensitive layer thus prepared, the half decay exposure amount by negative charging was measured in the same way as in Example 1. The $E_{50}$ value was 12 lux.sec.

Structure of Chlorodian Blue:

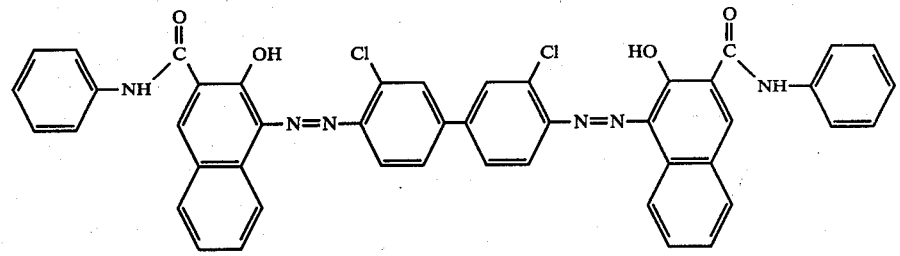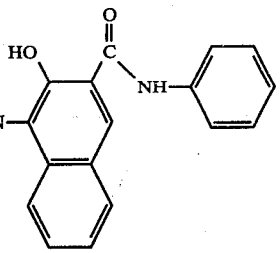

EXAMPLES 15-17

By following the same procedure as in Example 14 except that Compounds (2), (4) and (7) were used in place of Compound (1), double layer light-sensitive materials were prepared. On these samples, a half decay exposure amounts by negative charging were measured as in Example 1. The results are shown in the following table.

| Example | Compound | $E_{50}$ lux.sec. |
|---------|----------|-------------------|
| 15 | (2) | 18 |
| 16 | (4) | 14 |
| 17 | (7) | 17 |

While the invention has been described in detail and with reference to specific embodiments thereof, it will be apparent to one skilled in the art that various changes and modifications can be made therein without departing from the spirit and scope thereof.

What is claimed is:

1. An electrophotographic light-sensitive material comprising a conductive support having formed thereon a light-sensitive layer containing a compound selected from the group of compounds consisting of general formula I, II or III:

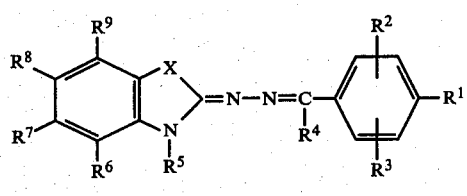 I

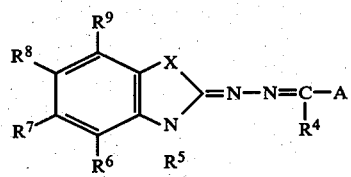 II

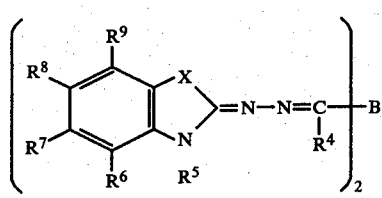 III wherein

X is an oxygen atom, a sulfur atom, a selenium atom, an imino group a substituted imino group, a methylene group or a substituted methylene group;

$R^1$ is an alkoxy group, an aralkyloxy group, or a substituted amino group shown by

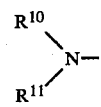

(wherein $R^{10}$ and $R^{11}$ independently are an alkyl group, a substituted alkyl group, a phenyl group, a substituted phenyl group or groups capable of forming a heterocyclic ring containing a nitrogen atom;

$R^2$ and $R^3$ independently are a hydrogen atom, a halogen atom, an alkyl group, or a lower alkoxy group;

$R^4$ is a hydrogen atom, an alkyl group, a phenyl group or a substituted phenyl group;

$R^5$ is an alkyl group or a substituted alkyl group;

$R^6$, $R^7$, $R^8$ and $R^9$, independently are an alkyl group, a substituted alkyl group, a phenyl group, a substituted phenyl group, an alkoxy group, a substituted alkoxy group, an aralkyloxy group, a substituted aralkyloxy group, a hydrogen atom, a halogen atom, or an amino group shown by

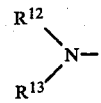

(wherein $R^{12}$ and $R^{13}$ are same as the groups shown by $R^{10}$ and $R^{11}$), or form a condensed carbon ring or a condensed heterocyclic ring by combining;

A is a monocyclic heterocyclic 5-membered ring, a condensed 5-membered heterocyclic ring or a condensed heterocyclic 6-membered ring shown by following formulae

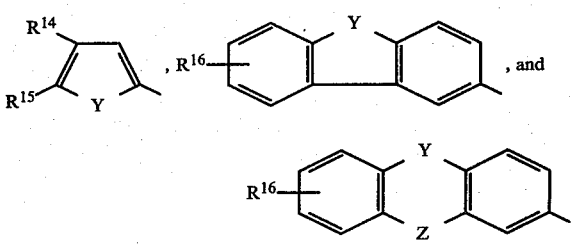

(wherein Y and Z independently are a sulfur atom, an oxygen atom, or N—R$^{17}$ and (wherein R$^{17}$ is an alkyl group having 1-4 carbon atoms); R$^{14}$ and R$^{15}$ are groups capable of forming a benzene ring or a naphthalene ring by combining; and R$^{16}$ is a hydrogen atom, substituted or unsubstituted alkyl groups, alkoxy groups, aryloxy groups, acyl groups, alkoxycarbonyl groups, aryloxycarbonyl groups, halogen atoms, monoalkylamino groups, dialkylamino group, amido groups, or nitro groups; and B is an aryl group or a substituted aryl group and wherein said electrophotographic material includes a charge generation material.

2. The electrophotographic light-sensitive material as claimed in claim 1 wherein the light-sensitive layer is comprised of said charge generating material.

3. The electrophotographic light-sensitive material as claimed in claim 2 wherein the light-sensitive layer contains a high molecular binder.

4. The electrophotographic light-sensitive material as claimed in claim 1 wherein the light-sensitive layer is comprised of a charge transporting layer containing at least one of the compounds shown by general formulae I, II and III and further containing the fine particles of a charge generating material dispersed therein.

5. The electrophotographic light-sensitive material as claimed in claim 1 wherein the light-sensitive layer is comprised of a charge generating layer containing a charge generating material as the main component and a charge transporting layer comprising a compound shown by general formulae I, II and III.

6. The electrophotographic light-sensitive material as claimed in claim 5 wherein the charge generating layer is disposed on the charge transporting layer.

7. The electrophotographic light-sensitive material as claimed in claim 5 wherein the charge transporting layer is disposed on the charge generating layer.

8. The electrophotographic light-sensitive material as claimed in claim 3 wherein the amount of the high molecular binder is 0.8-4 parts by weight per one part by weight of the compound shown by general formula I, II or III.

9. The electrophotographic light-sensitive material as claimed in claim 5 wherein an interlayer is formed between the conductive support and the light-sensitive layer.

10. An electrophotographic light-sensitive material comprising a conductive support having formed thereon a light-sensitive layer containing a compound selected from the group of compounds consisting of general formula II or III:

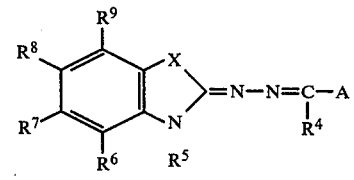

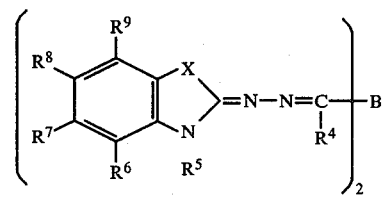

wherein
X is an oxygen atom, a sulfur atom, a selenium atom, an imino group a substituted imino group,
R$^4$ is a hydrogen atom, an alkyl group, a phenyl group or a substituted phenyl group;
R$^5$ is an alkyl group or a substituted alkyl group;
R$^6$, R$^7$, R$^8$ and R$^9$, independently are an alkyl group, a substituted alkyl group, a phenyl group, a substituted phenyl group, an alkoxy group, a substituted alkoxy group, an aralkyloxy group, a substituted aralkyloxy group, a hydrogen atom, a halogen atom, or an amino group shown by

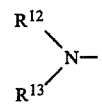

(wherein R$^{12}$ and R$^{13}$ are same as the groups shown by R$^{10}$ and R$^{11}$), or form a condensed carbon ring or a condensed heterocyclic ring by combining;
A is a monocyclic heterocyclic 5-membered ring, a condensed 5-membered heterocyclic ring or a condensed heterocyclic 6-membered ring shown by following formulae

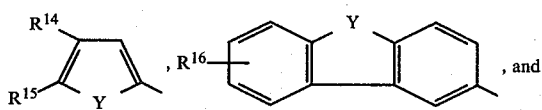

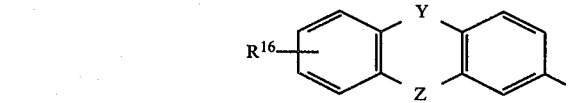

(wherein Y and Z independently are a sulfur atom, an oxygen atom, or N—R$^{17}$ (wherein R$^{17}$ is an alkyl group having 1-4 carbon atoms); R$^{14}$ and R$^{15}$ are groups capable of forming a benzene ring or a naphthalene ring by combining; R$^{16}$ is a hydrogen atom, substituted or unsubstituted alkyl groups, alkoxy groups, aryloxy groups, acyl groups, alkoxycarbonyl groups, aryloxycarbonyl groups, halogen atoms, monoalkylamino groups, dialkylamino group, amido groups, or nitro groups; and
B is an aryl group or a substituted aryl group.

* * * * *